(12) United States Patent
Creighton, IV

(10) Patent No.: US 7,603,905 B2
(45) Date of Patent: Oct. 20, 2009

(54) MAGNETIC NAVIGATION AND IMAGING SYSTEM

(75) Inventor: Francis M. Creighton, IV, St. Louis, MO (US)

(73) Assignee: Stereotaxis, Inc., St. Louis, MO (US)

( * ) Notice: Subject to any disclaimer, the term of this patent is extended or adjusted under 35 U.S.C. 154(b) by 563 days.

(21) Appl. No.: 11/483,397

(22) Filed: Jul. 7, 2006

(65) Prior Publication Data

US 2007/0038064 A1   Feb. 15, 2007

Related U.S. Application Data

(60) Provisional application No. 60/697,822, filed on Jul. 8, 2005.

(51) Int. Cl.
*A61N 2/00* (2006.01)
*A61B 8/14* (2006.01)

(52) U.S. Cl. .................. 73/602; 600/437; 600/114; 600/9; 128/899

(58) Field of Classification Search .................. 600/407; 73/602; 128/899
See application file for complete search history.

(56) References Cited

U.S. PATENT DOCUMENTS

| | | | |
|---|---|---|---|
| 5,654,864 A | 8/1997 | Ritter et al. |
| 5,931,818 A | 8/1999 | Werp et al. |
| 6,014,580 A | 1/2000 | Blume et al. |
| 6,015,414 A | 1/2000 | Werp et al. |
| 6,128,174 A | 10/2000 | Ritter et al. |
| 6,148,823 A | 11/2000 | Hastings |
| 6,152,933 A | 11/2000 | Werp et al. |
| 6,157,853 A | 12/2000 | Blume et al. |
| 6,212,419 B1 | 4/2001 | Blume et al. |
| 6,241,671 B1 | 6/2001 | Ritter et al. |
| 6,292,678 B1 | 9/2001 | Hall et al. |
| 6,296,604 B1 | 10/2001 | Garibaldi et al. |
| 6,298,257 B1 | 10/2001 | Hall et al. |
| 6,304,768 B1 | 10/2001 | Blume et al. |
| 6,315,709 B1 | 11/2001 | Garibaldi et al. |
| 6,330,467 B1 | 12/2001 | Creighton, IV et al. |
| 6,352,363 B1 | 3/2002 | Munger et al. |
| 6,364,823 B1 | 4/2002 | Garibaldi et al. |
| 6,375,606 B1 | 4/2002 | Garibaldi et al. |
| 6,385,472 B1 | 5/2002 | Hall et al. |
| 6,401,723 B1 | 6/2002 | Garibaldi et al. |

(Continued)

*Primary Examiner*—David A. Rogers
*Assistant Examiner*—Rose M Miller
(74) *Attorney, Agent, or Firm*—Harness, Dickey & Pierce, P.L.C.

(57) ABSTRACT

A system for imaging and magnetically navigating a medical device within an operating region in a subject's body includes a first C-arm and a second C-arm. The system includes an imaging beam source and an imaging beam receiver mounted on the first C-arm disposed on opposite sides of the operating region to image the operating region. The system includes a pair of magnetic pods, which are movably mounted on either the first or second C-arm. The magnetic pods are movable between an imaging position and a navigating position in which the pods are disposed on opposite sides of the operating region in the same plane as at least one imaging beam source. The second C-arm is movable between an imaging position in which the imaging beam source and imaging beam receiver on the second C-arm is positioned so that the imaging beam sources and receivers are in the same plane.

20 Claims, 18 Drawing Sheets

U.S. PATENT DOCUMENTS

| | | |
|---|---|---|
| 6,428,551 B1 | 8/2002 | Hall et al. |
| 6,459,924 B1 | 10/2002 | Creighton, IV et al. |
| 6,505,062 B1 | 1/2003 | Ritter et al. |
| 6,507,751 B2 | 1/2003 | Blume et al. |
| 6,522,909 B1 | 2/2003 | Garibaldi et al. |
| 6,524,303 B1 | 2/2003 | Garibaldi |
| 6,527,782 B2 | 3/2003 | Hogg et al. |
| 6,537,196 B1 | 3/2003 | Creighton, IV et al. |
| 6,542,766 B2 | 4/2003 | Hall et al. |
| 6,562,019 B1 | 5/2003 | Sell |
| 6,630,879 B1 | 10/2003 | Creighton, IV et al. |
| 6,662,034 B2 | 12/2003 | Segner et al. |
| 6,677,752 B1 | 1/2004 | Creighton, IV et al. |
| 6,702,804 B1 | 3/2004 | Ritter et al. |
| 6,733,511 B2 | 5/2004 | Hall et al. |
| 6,755,816 B2 | 6/2004 | Ritter et al. |
| 6,817,364 B2 | 11/2004 | Garibaldi et al. |
| 6,834,201 B2 | 12/2004 | Gillies et al. |
| 6,902,528 B1 | 6/2005 | Garibaldi et al. |
| 6,911,026 B1 | 6/2005 | Hall et al. |
| 6,968,846 B2 | 11/2005 | Viswanathan |
| 6,975,197 B2 | 12/2005 | Creighton, IV |
| 6,980,843 B2 | 12/2005 | Eng et al. |
| 7,008,418 B2 | 3/2006 | Hall et al. |
| 7,010,338 B2 | 3/2006 | Ritter et al. |
| 7,019,610 B2 | 3/2006 | Creighton, IV et al. |
| 7,020,512 B2 | 3/2006 | Ritter et al. |
| 7,066,924 B1 | 6/2006 | Garibaldi et al. |
| 7,313,429 B2 * | 12/2007 | Creighton et al. ............ 600/427 |
| 2001/0038683 A1 | 11/2001 | Ritter et al. |
| 2002/0019644 A1 | 2/2002 | Hastings et al. |
| 2002/0177789 A1 | 11/2002 | Ferry et al. |
| 2004/0006301 A1 | 1/2004 | Sell et al. |
| 2004/0019447 A1 | 1/2004 | Shachar |
| 2004/0064153 A1 | 4/2004 | Creighton, IV et al. |
| 2004/0068173 A1 | 4/2004 | Viswanathan |
| 2004/0096511 A1 | 5/2004 | Harburn et al. |
| 2004/0133130 A1 | 7/2004 | Ferry et al. |
| 2004/0157082 A1 | 8/2004 | Ritter et al. |
| 2004/0158972 A1 | 8/2004 | Creighton, IV et al. |
| 2004/0186376 A1 | 9/2004 | Hogg et al. |
| 2004/0199074 A1 | 10/2004 | Ritter et al. |
| 2004/0249262 A1 | 12/2004 | Werp et al. |
| 2004/0249263 A1 | 12/2004 | Creighton, IV |
| 2004/0260172 A1 | 12/2004 | Ritter et al. |
| 2005/0020911 A1 | 1/2005 | Viswanathan et al. |
| 2005/0043611 A1 | 2/2005 | Sabo et al. |
| 2005/0065435 A1 | 3/2005 | Rauch et al. |
| 2005/0096589 A1 | 5/2005 | Shachar |
| 2005/0113628 A1 | 5/2005 | Creighton, IV et al. |
| 2005/0113812 A1 | 5/2005 | Viswanathan et al. |
| 2005/0119687 A1 | 6/2005 | Dacey, Jr. et al. |
| 2005/0182315 A1 | 8/2005 | Ritter et al. |
| 2005/0187424 A1 * | 8/2005 | Hambuchen et al. ............ 600/12 |
| 2005/0256398 A1 | 11/2005 | Hastings et al. |
| 2006/0009735 A1 | 1/2006 | Viswanathan et al. |
| 2006/0025679 A1 | 2/2006 | Viswanathan et al. |
| 2006/0036125 A1 | 2/2006 | Viswanathan et al. |
| 2006/0036163 A1 | 2/2006 | Viswanathan |
| 2006/0041178 A1 | 2/2006 | Viswanathan et al. |
| 2006/0041179 A1 | 2/2006 | Viswanathan et al. |
| 2006/0041180 A1 | 2/2006 | Viswanathan et al. |
| 2006/0041181 A1 | 2/2006 | Viswanathan et al. |
| 2006/0041245 A1 | 2/2006 | Ferry et al. |
| 2006/0058646 A1 | 3/2006 | Viswanathan |
| 2006/0074297 A1 | 4/2006 | Viswanathan |
| 2006/0079745 A1 | 4/2006 | Viswanathan |
| 2006/0079812 A1 | 4/2006 | Viswanathan |
| 2006/0093193 A1 | 5/2006 | Viswanathan |
| 2006/0094956 A1 | 5/2006 | Viswanathan |
| 2006/0100505 A1 | 5/2006 | Viswanathan |
| 2006/0114088 A1 | 6/2006 | Shachar |
| 2006/0116633 A1 | 6/2006 | Shachar |
| 2006/0144407 A1 | 7/2006 | Aliberto et al. |
| 2006/0144408 A1 | 7/2006 | Ferry |
| 2009/0062646 A1 * | 3/2009 | Creighton et al. ............ 600/437 |

* cited by examiner

MAGNETIC NAVIGATION AND IMAGING SYSTEM

CROSS-REFERENCE TO RELATED APPLICATIONS

This application claims the benefit of U.S. Provisional Patent Application Ser. No. 60/697,822 filed on Jul. 8, 2005, the entire disclosure of which are incorporated herein by reference.

FIELD OF THE INVENTION

This invention relates to a magnetic surgery system, and in particular to an open magnetic surgery system that provides greater access to the patient for imaging and other purposes.

BACKGROUND OF THE INVENTION

A wide variety of minimally invasive surgical procedures have been developed which employ catheters, endoscopes, or other similar devices that can be navigated remotely from their distal ends. The catheter, endoscope or other medical device is manipulated through the tissue or through an existing body lumen or cavity using a guide wire or other mechanical means. Examples of such procedures include the treatment of aneurysms, arterial ventricular malformations, atrial fibrillation, ureteral stones, and investigations of lumen such as sigmoidoscopies and colonoscopies, ERCP's; and biliary duct examinations. While these procedures are highly beneficial to the patient, they are difficult and time consuming for the physician. Some procedures can only be performed by the most skilled surgeons.

Because of the small size of the vessels to be navigated, extremely high resolution and flexibly moveable fluoroscopes are needed to provide adequate imaging. These fluoroscopes are large instruments. Even now, accessibility of adequate imaging in the presence of equipment needed to navigate the catheters, endoscopes, or other similar devices through the vessels.

Systems have been disclosed for magnetic guidance of catheters and guidewires to facilitate navigation of difficult vascular turns. Imaging means can be used in conjunction with magnetically guided surgery. An example of such a system is described in U.S. utility patent application Ser. No. 09/020,798, filed Feb. 9, 1998, entitled "Device and Method for Specifying Magnetic Field for Surgical Applications," now U.S. Pat. No. 6,014,580. While magnetically guided surgery with such systems is practical, the sheer bulk and size of their magnetic systems results in less accessibility of the operating region of the patient than a surgeon might prefer. Also, imaging equipment (such as X-ray equipment) for observing the operating region has been fixed to the magnetic system assembly, or otherwise been immobile or of limited mobility relative to the magnets and/or the patient. This relative immobility tends to reduce the ability of the surgeons to see the medical operating device within the patient, making the operation somewhat more difficult for the surgeon and somewhat riskier for the patient than might otherwise be the case. It would therefore be desirable to provide an apparatus for magnetically-assisted surgery that provides flexibility of both the imaging and of the magnetic field application.

A difficulty associated with magnetic guidance is that the magnetic field source needed to guide the medical devices within small vessels and body lumens may be relatively large. The distance between the magnet field source and the operating region is also a factor in providing a system for applying magnetic fields for navigation, while maintaining an "openness" and accessibility of imaging systems as described above.

SUMMARY OF THE INVENTION

Embodiments of the systems of the present invention advance the art of simultaneous imaging and remote surgical navigation by combining navigation and imaging system equipment in a manner that improves flexibility and accessibility of both systems. In one embodiment of the present invention, a system for imaging and magnetically navigating a medical device within an operating region in a subject's body is provided that comprises a first C-arm and a second C-arm. The system comprises an imaging beam source and an imaging beam receiver mounted on the first C-arm and positioned to be disposed on opposite sides of the operating region to image the operating region. The system further comprises an imaging beam source and an imaging beam receiver mounted on the second C-arm and positionable to be disposed on opposite sides of the operating region to image the operating region. In this embodiment, the second C-arm is movable between an imaging position in which the imaging beam source and imaging beam receiver on the second C-arm is positioned so that the imaging beam sources and receivers are in the same plane, and a stowed position in which the second C-arm is in a navigating position. The system comprises a pair of magnetic pods movably mounted on the first C-arm, the magnetic pods being movable between a navigating position in which the pods are disposed on opposite sides of the operating region in the same plane as the imaging beam source and the imaging beam receiver, for applying a navigating magnetic field of at least 0.08 T in any direction to the operating region, and a stowed position in which the magnets are moved out of the plane to accommodate the imaging beam source and imaging beam receiver on the second C-arm in its imaging position. The imaging beam source and the imaging beam receiver on the first C-arm are positioned so that a line between the imaging beam source and receive is generally perpendicular to, and coplanar with a line between the magnet pods in their navigating position.

In another aspect of the present invention, a second embodiment of a system provides for quickly moving between a position for navigation operation and a position for imaging. In the second embodiment, the system comprises a first C-arm, and a second C-arm having an imaging beam source and beam receiver mounted generally adjacent the magnet pods, such that the second C-arm may move from a navigation position utilizing the magnet pods to an imaging position utilizing the imaging beam source and beam receiver. The system comprises an imaging beam source and an imaging beam receiver mounted on the first C-arm so that the imaging beam source and imaging beam receiver can be disposed on opposite sides of the operating region in the subject. The system also comprises a second C-arm movable relative to the first C-arm between a stowed position and an imaging position, and having an imaging beam source and an imaging beam receiver mounted on the second C-arm. When the second C-arm is in its imaging position, the imaging beam source and imaging beam receiver are disposed on opposite sides of the operating region, in substantially the same plane as the imaging beam source and imaging beam receiver on the first C-arm. The second C-arm comprises a pair of magnetic pods mounted on the first C-arm, the C-arm being movable between a navigating position in which the pods are disposed on opposite sides of the operating region in the same plane as the imaging beam source and the imaging beam receiver, for applying a navigating magnetic field of at least 0.08 T in any direction to the operating region, and a stowed position in which the magnets are not on opposite sides of the operating region to accommodate the imaging beam source and imaging beam receiver on the second C-arm in its imaging position. When in the stowed position, the imaging beam source and the imaging beam receiver on the second C-arm are positioned so that a line between the imaging beam source and receiver is generally perpendicular to, and coplanar with a line between the magnet pods in their navigating position.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

Corresponding reference numerals indicate corresponding parts throughout the several views of the drawings.

DETAILED DESCRIPTION OF THE EMBODIMENTS

The following description of the various embodiment(s) are merely exemplary in nature and are in no way intended to limit the invention, its application, or uses.

Figure 1:
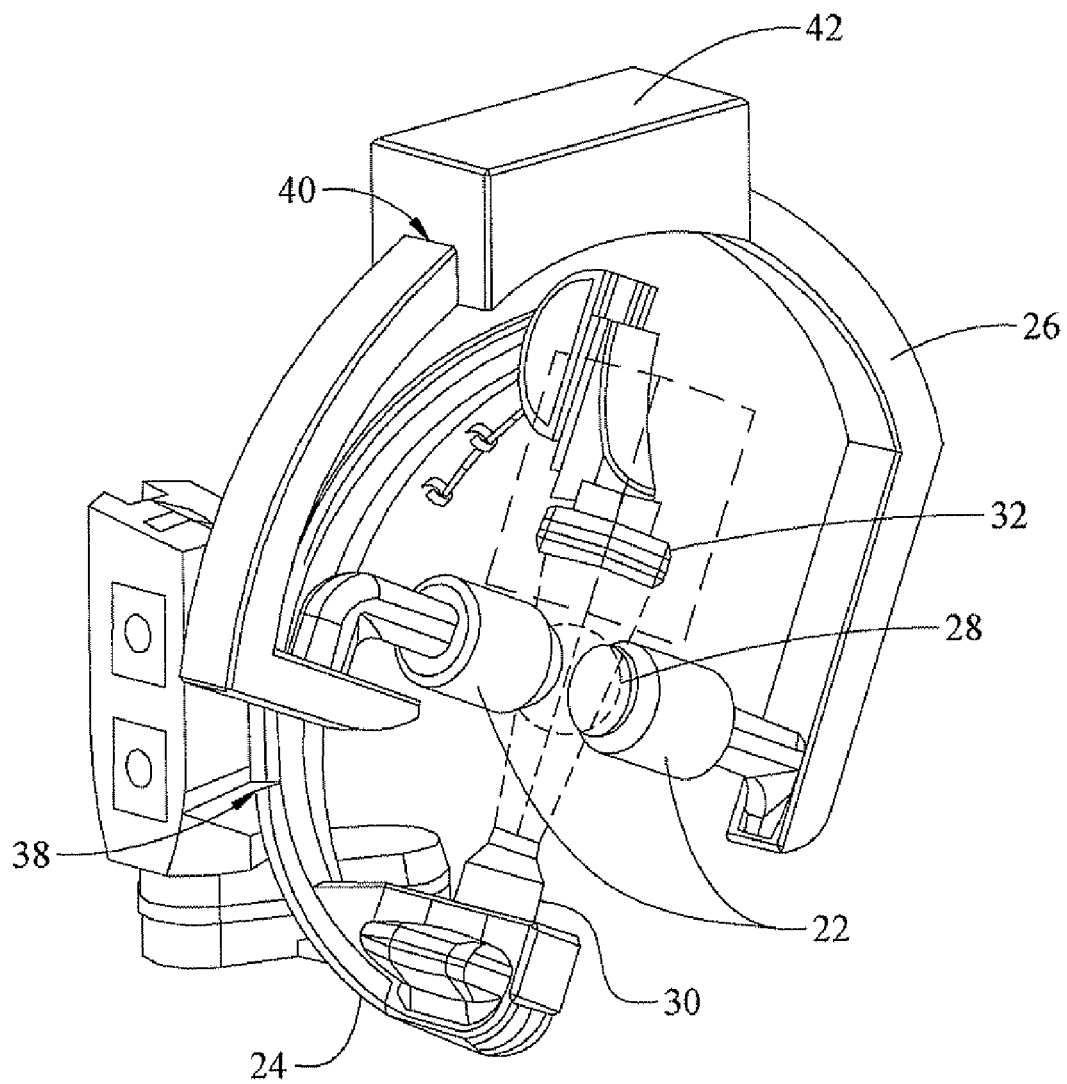
FIG. 1 is an isometric view of a first embodiment of magnetic navigation and imaging system, showing the first C-arm having an imaging beam and imaging receiver, and a second C-arm having magnet pods perpendicular to the imaging beam.
Figure 2:
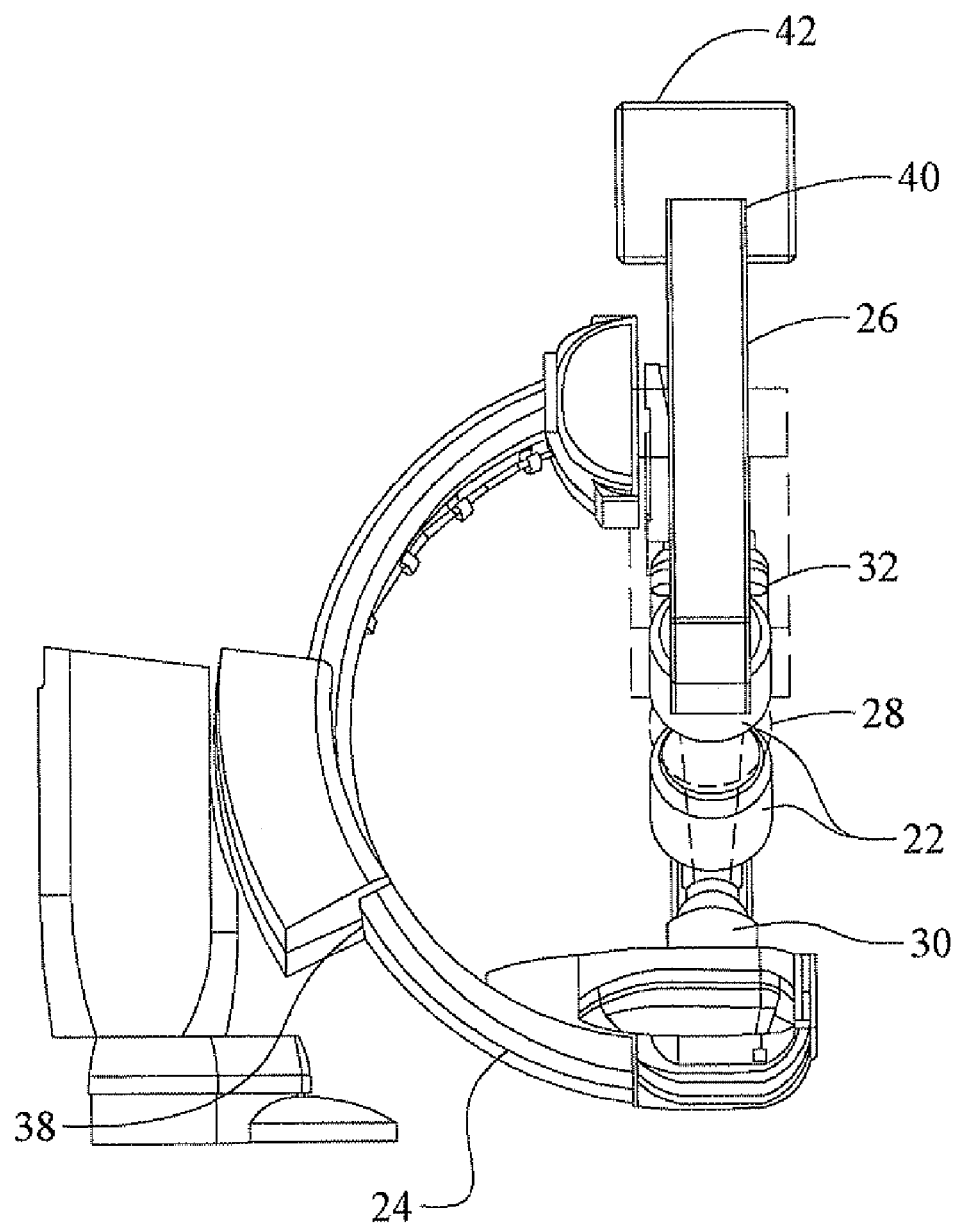
FIG. 2 is a side elevation view of the system of the first embodiment.

In one first embodiment of the present invention, a system that enables both imaging and magnetic navigation within an operating region of a subject's body is provided. The system comprises magnetic navigational equipment 22 that provides navigation control in an operating region 28 of a subject's body, as well as imaging equipment for procedures where anatomical views of the patient may be required during the procedure. The system generally comprises a first imaging equipment support structure having a generally C-shaped configuration 24, and a second equipment support structure having a generally C-shaped configuration 26. The first and second C-arm structures are preferably mounted on tracks that enable the C-arms to rotate circumferentially about an operating region 28 of the subject's body as shown in FIG. 1.

In the first embodiment, the system comprises a first C-arm 24 with an imaging beam source 30 and an imaging beam receiver 32 that are mounted on the first C-arm 24 and positioned to be disposed on opposite sides of the operating region 28 for imaging the operating region. The imaging beam receiver 32 may be configured to accommodate an imaging plate of approximately 20 centimeters, and may preferably accommodate an imaging plate of up to approximately 30 centimeters. The operating region 28 is represented by a sphere of approximately 12 inch diameter as shown in FIG. 1, which represents a patient's head plus 1 inch of additional clearance. The system also comprises a second C-arm 26 having magnetic navigational equipment 22 mounted thereon, which magnetic navigational equipment is positionable to be disposed on opposite sides of the operating region 28 to image the operating region. The first C-arm 24 and second C-arm 26 are movably mounted via tracks 38 and 40, to permit coordinated simultaneous rotation of the first C-arm 24 and the second C-arm 26 in a generally circumferential arc about the operating region 28 of the subject's body as shown in FIG. 1. The first and second C-arms may be controllably rotated about the patient by a servo drive motor mechanisms preferably controlled by a computer system that is integrated with both the imaging and navigational equipment. In this manner, the computer control of the imaging and navigational equipment may provide for seamless coordination of movement of both systems to provide either imaging operation, navigation control or both. The first C-arm 24 comprises an imaging beam source 34 and imaging beam receiver 36 that are positioned so that they are in the same plane as the magnetic navigational pods 22 on the second C-arm 26. The magnetic pods 22 are disposed on the second C-arm 26 on opposite sides of the operating region 28, such that a line between the magnetic pods 22 is generally perpendicular to, and coplanar with a line between the imaging beam source 30 and the imaging beam receiver 32 mounted on the first C-arm 24. The magnetic pods 22 are capable of applying a navigating magnetic field of at least 0.08 T in any direction to the operating region 28. The pair of magnetic pods 22 are preferably positioned relative to each other to provide a 12 inch pod-to-pod separation. Such separation permits the magnetic navigation equipment to be utilized for INR or Neurosurgery therapies. The magnetic pods 22 each have a weight of approximately 120 pounds. The second C-arm 26 provides a minimum articulation of the magnetic pods 22 to ensure compatibility with secondary imaging equipment.

The first C-arm 24 is preferably mounted on a track 38 for enabling the C-arm to rotate about the radial center of the first C-arm 24, such that the first C-arm 24 rotates in a generally circumferential arc about the operating region 28. The track 38 is preferably mounted to a base unit having a drive mechanism for controlling the rotation of the first C-arm 24 about the operating region. In the first embodiment, a standing C-arm imaging system is provided as shown in FIG. 1. The C-arm shown is preferably a standing Siemens C-arm imaging system, but may alternatively be any equivalent imaging system capable of rotation about an operating region of a patient. The base unit for the first C-arm may be positioned on the floor in a location relative to a horizontal support table 44 for the patient, such that a portion of the patient's body on the patient support table 44 is within the operating region 28. The horizontal patient support table 44 is preferably movable in a direction along the longitudinal axis of the patient, to allow for positioning a desired area of the subject's body within the operating region 28.

The first embodiment further comprises a second C-arm 26 that is mounted on a track support 40 for enabling the second C-arm to rotate about the radial center of the second C-arm 24. The second C-arm 24 rotates in a generally circumferential arc about the operating region 28. The track support 40 is preferably mounted via a motorized trolley or travel mechanism to an overhead linear track that is parallel to the longitudinal axis of the patient and/or support table. The overhead linear track comprises a pair of magnetic navigational pods that are disposed or mounted at the ends of the second C-arm such that a line between the imaging beam source 30 and receiver 32 on the first C-arm 24 is generally perpendicular to, and coplanar with a line between the magnetic navigational pods 22 mounted on the second C-arm 26. The second C-arm 26 shown in FIG. 1 is an overhead secondary Siemens C-arm, but may alternatively be any equivalent system capable of rotation about an operating region of a patient.

Figure 3:
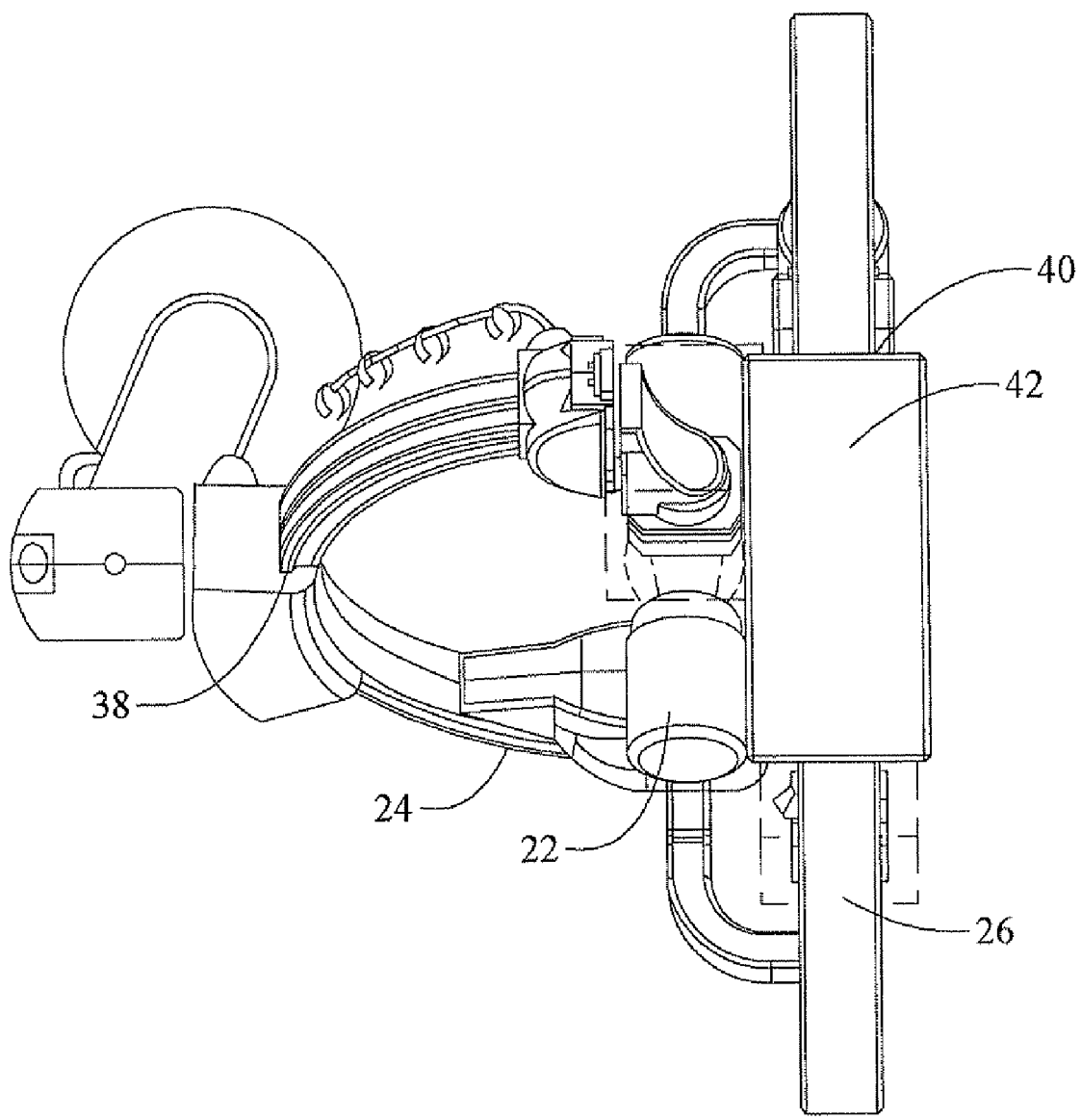
FIG. 3 is a top end elevation view of a magnetic navigation and imaging system of a second embodiment.
Figure 4:
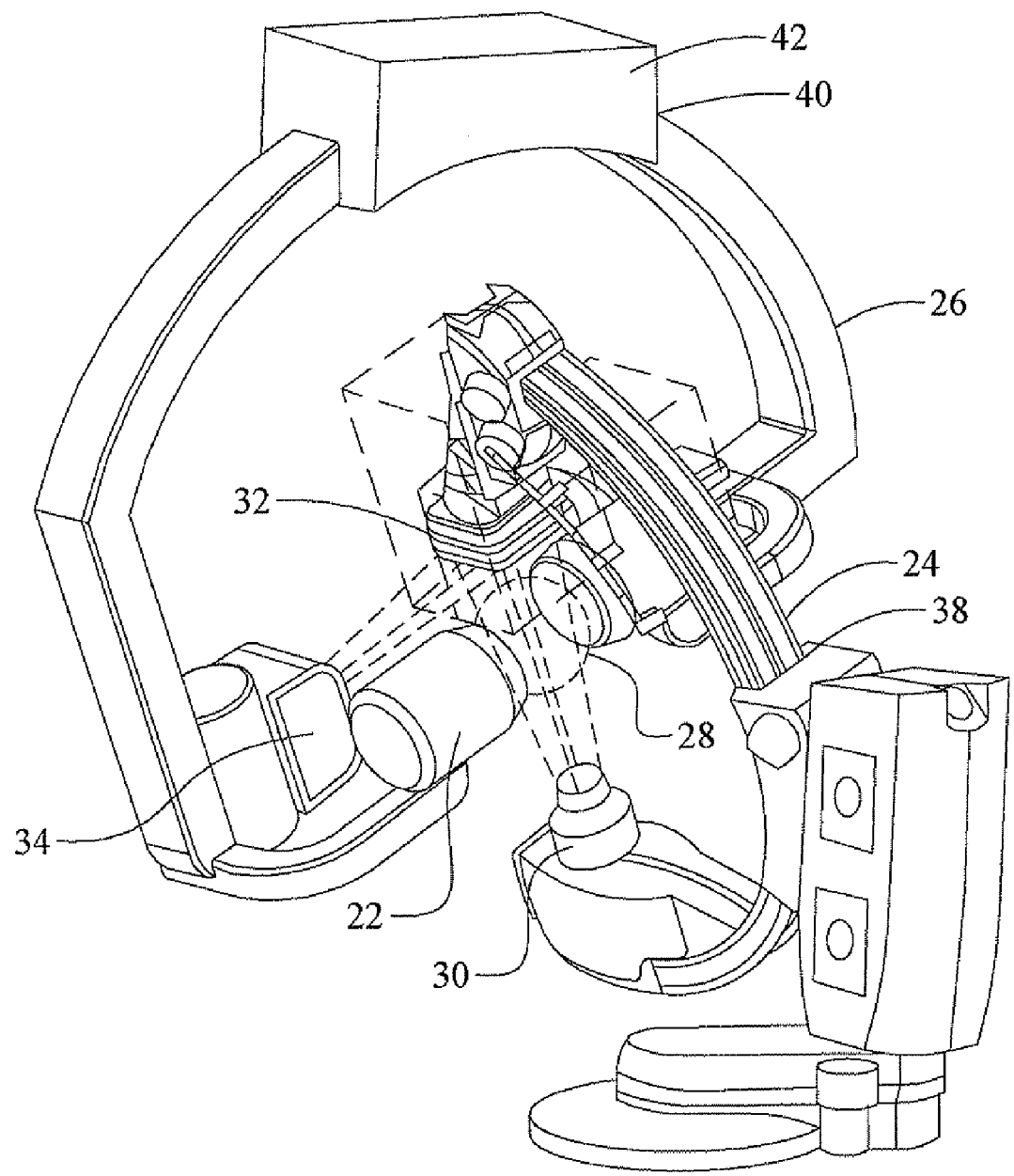
FIG. 4 is an isometric view of the system of the second embodiment, showing the magnet pods on the second C-arm perpendicular to the imaging beam and imaging receiver on the second C-arm.
Figure 5:
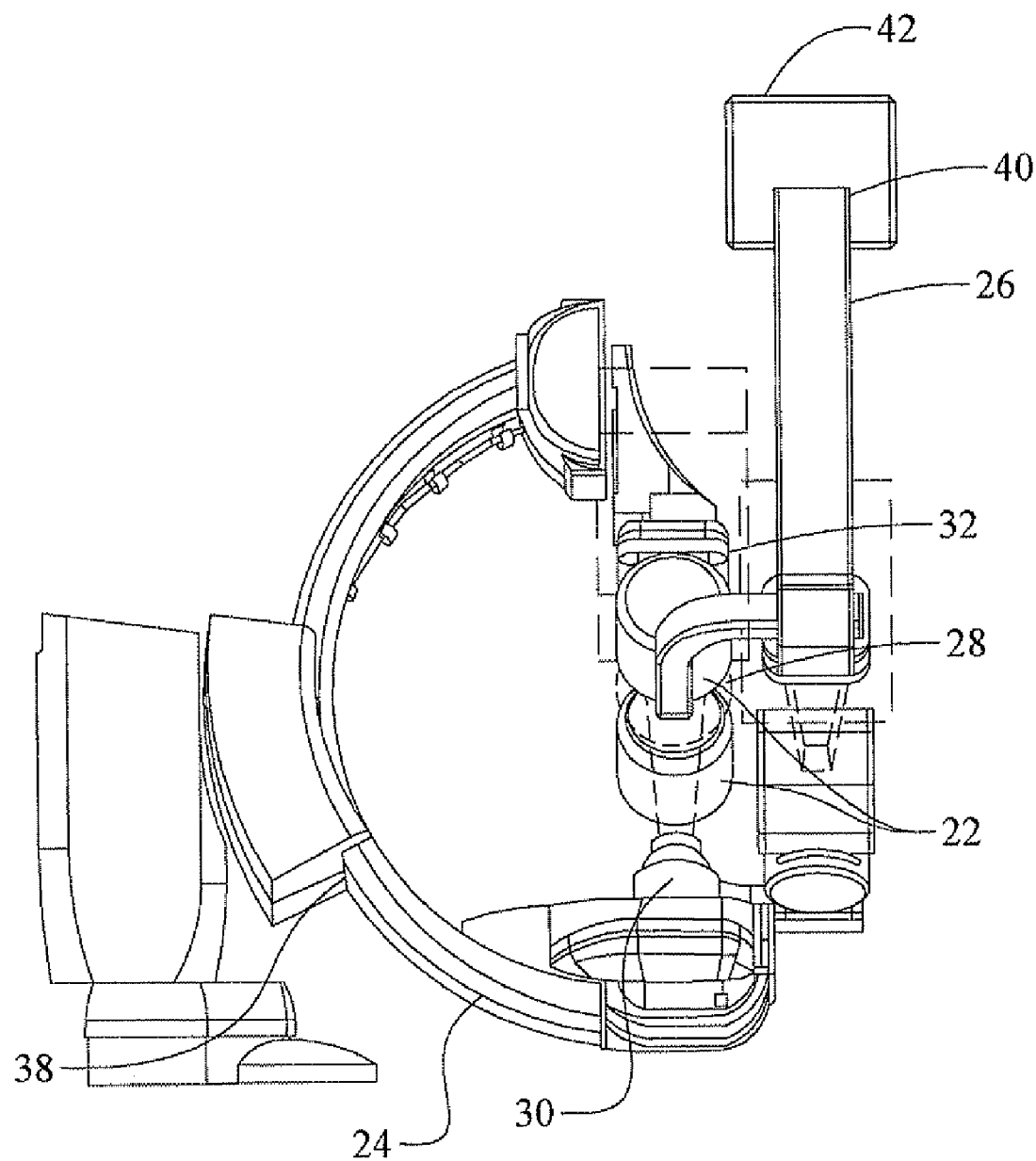
FIG. 5 is a side elevation view of the system of the second embodiment shown in FIG. 4.
Figure 6:
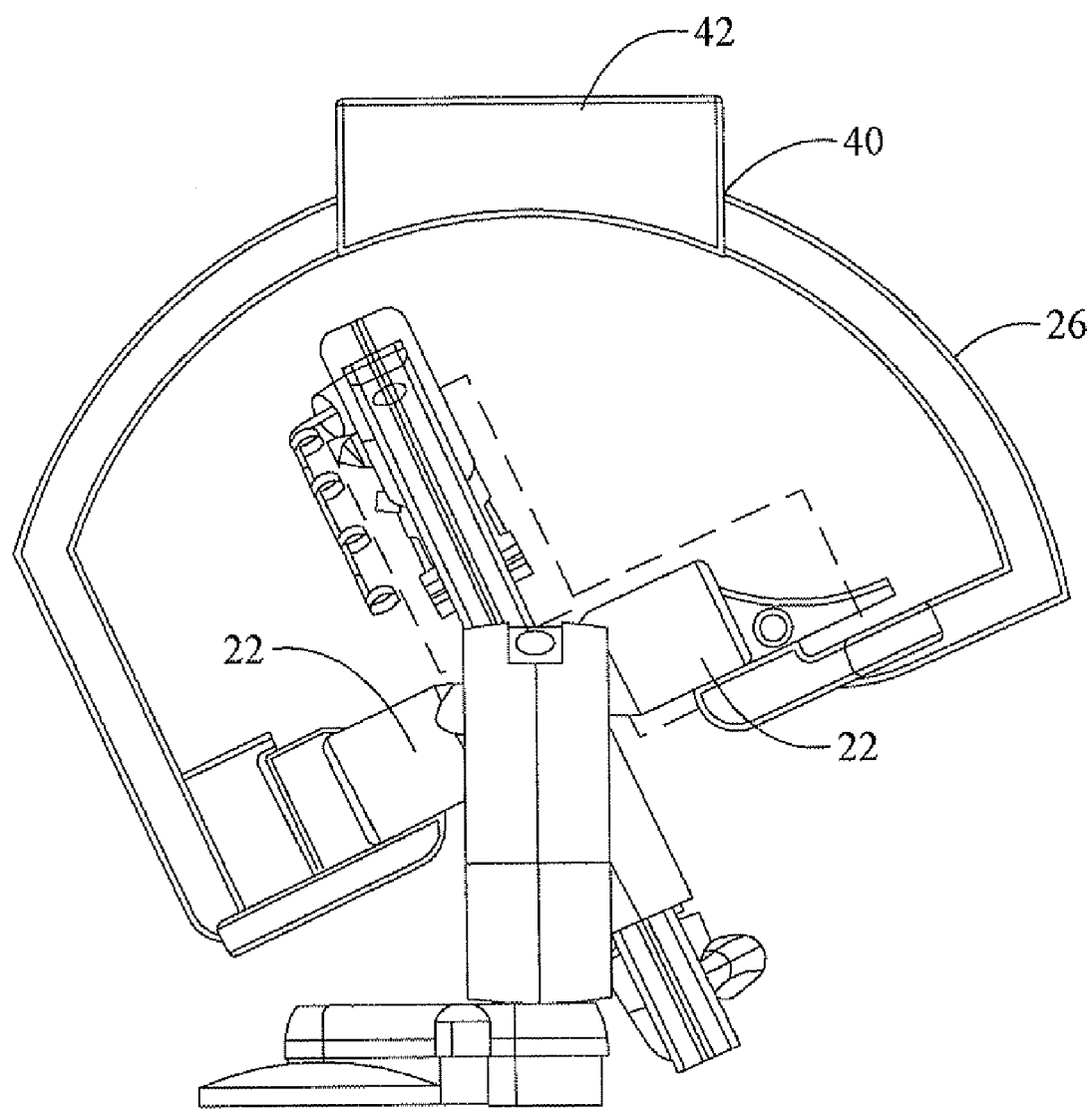
FIG. 6 is a rear end elevation view of the system of the second embodiment shown in FIG. 4.
Figure 7:
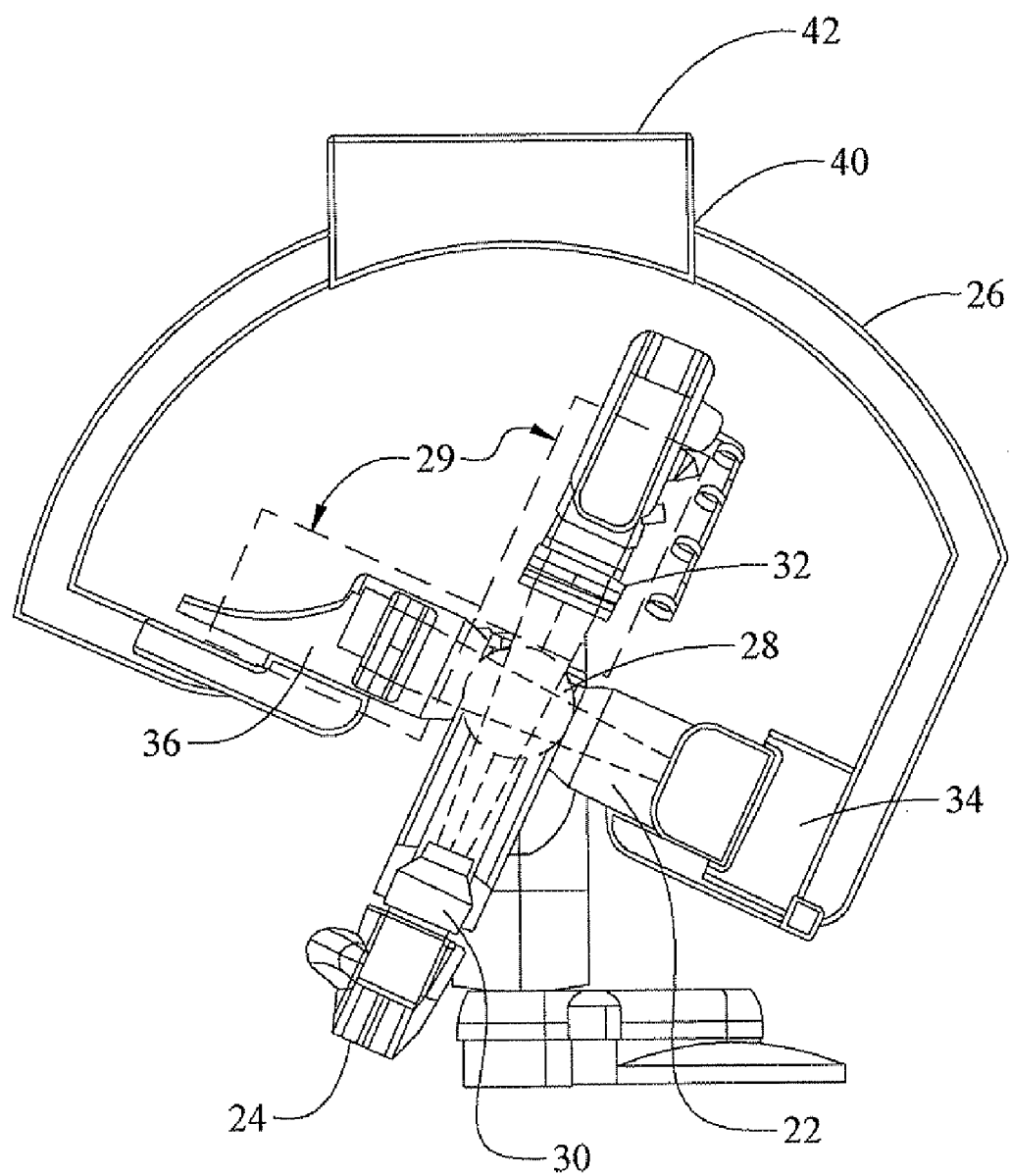
FIG. 7 is a front elevation view of the system of the second embodiment.
Figure 8:
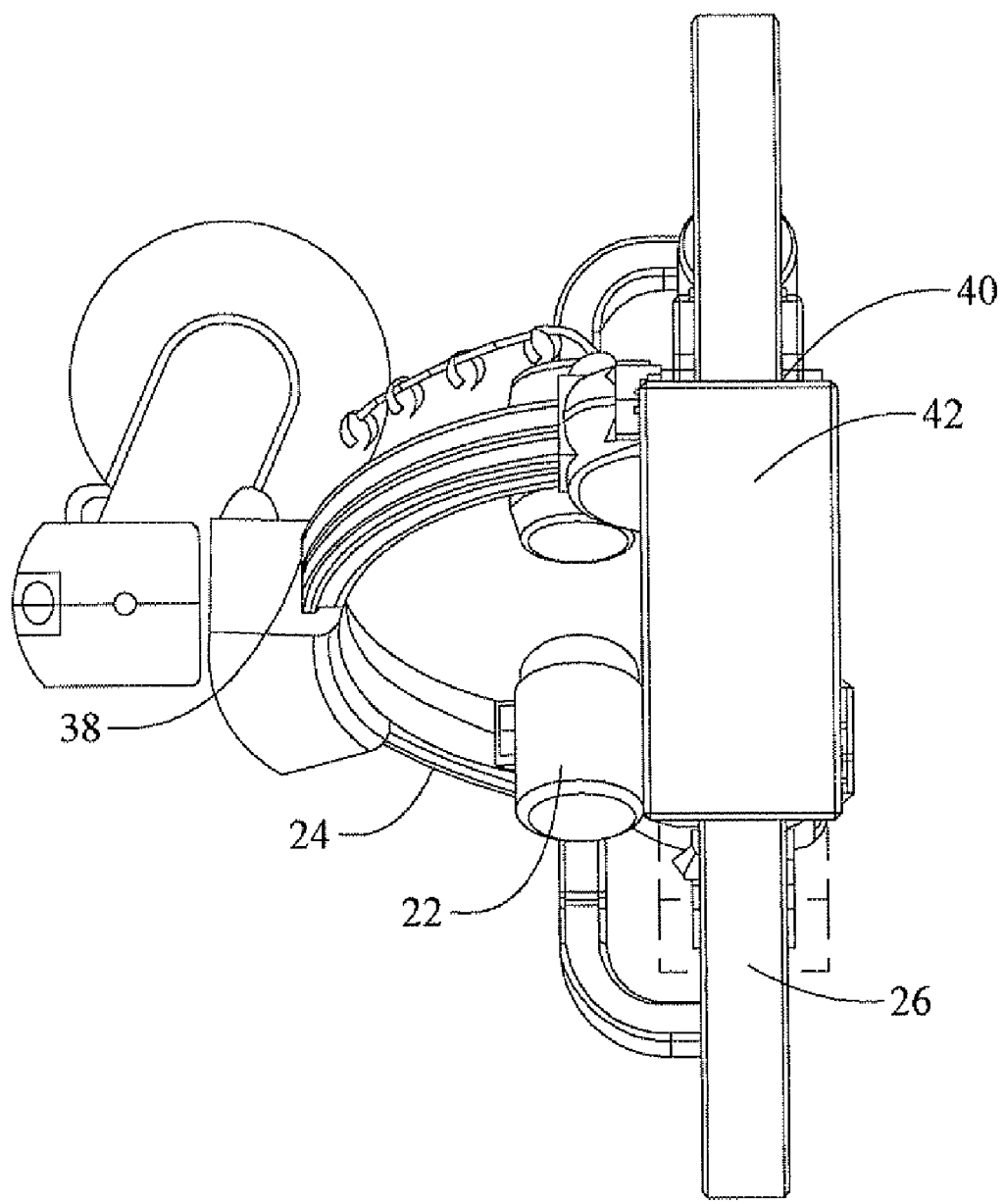
FIG. 8 is a top end elevation view of the system of the second embodiment.
Figure 9:
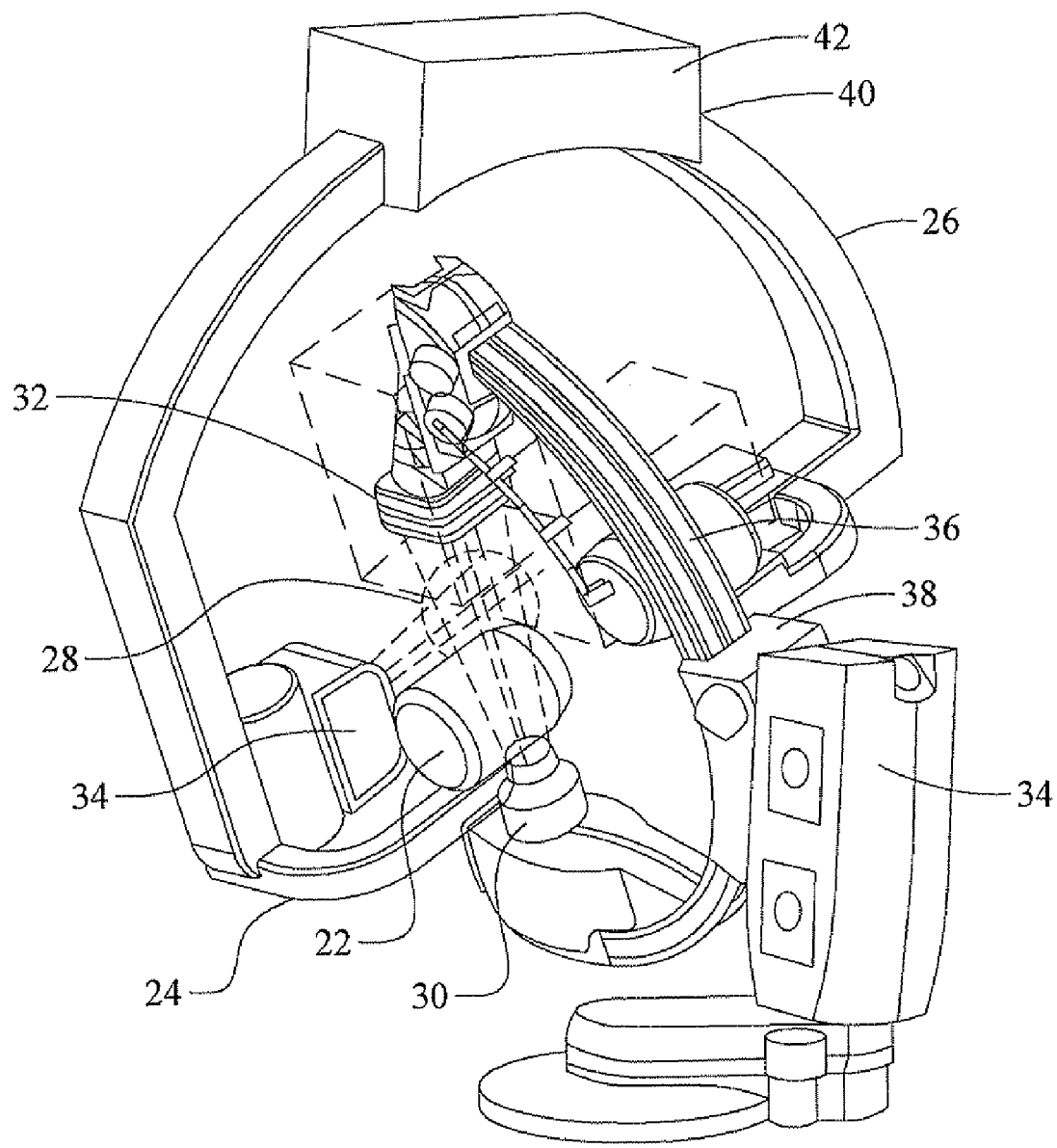
FIG. 9 is a front perspective view of the system of the second embodiment, showing the first C-arm having an imaging beam and imaging receiver, and a second C-arm having magnet pods perpendicular to the imaging beam.
Figure 10:
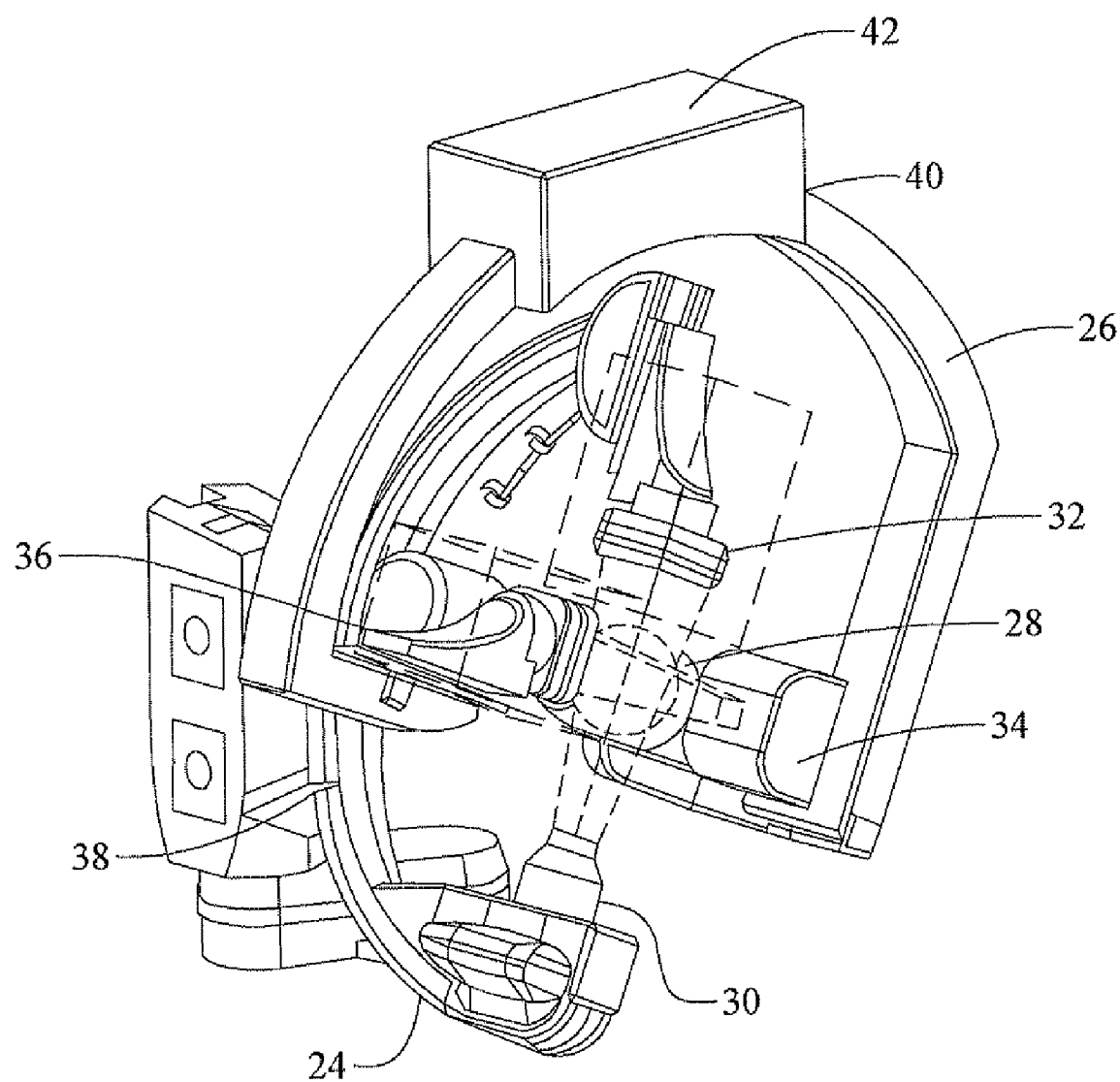
FIG. 10 is the system shown in FIG. 9 viewed from a rear perspective view.
Figure 11:
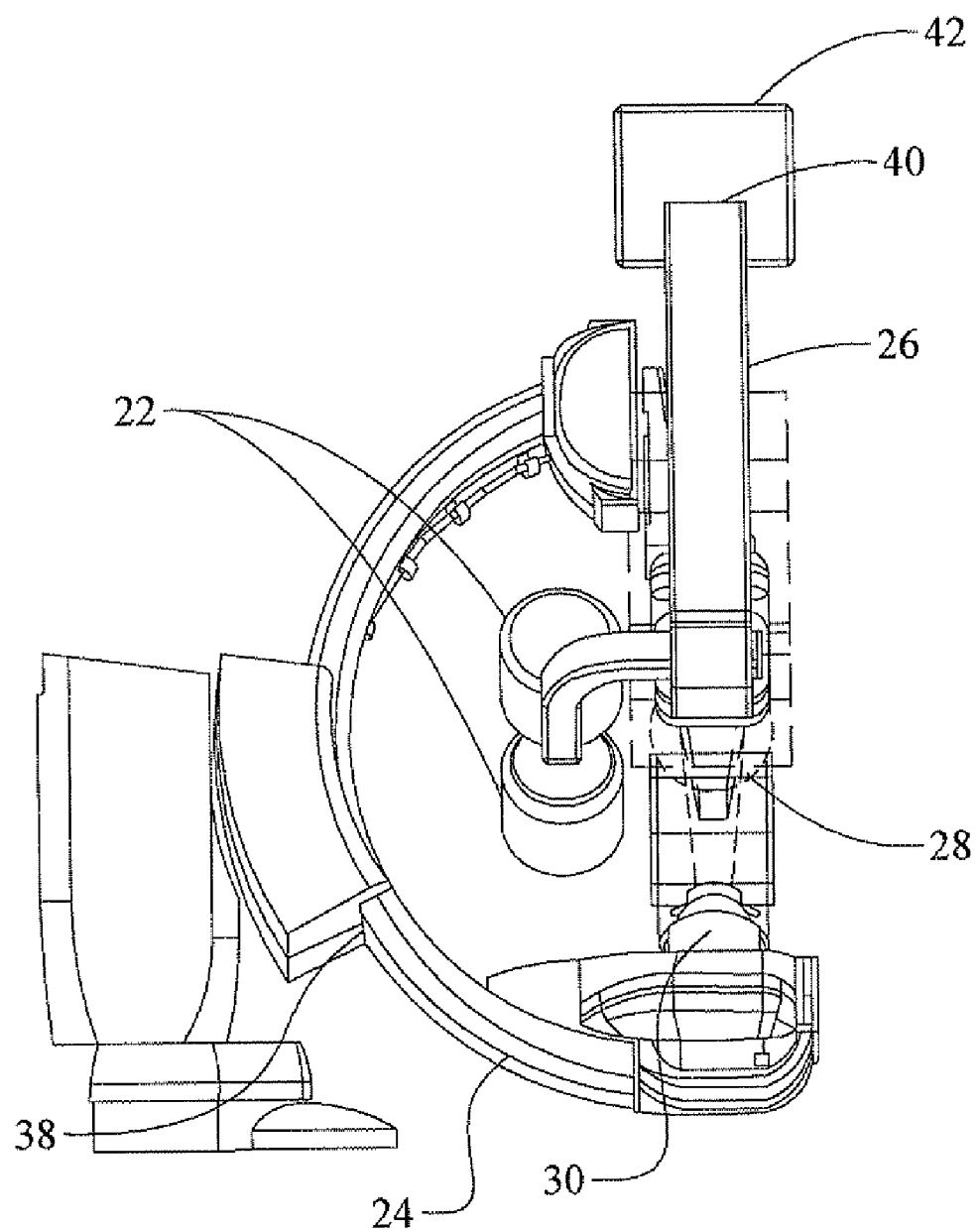
FIG. 11 is a side elevation view of the system of the second embodiment in accordance with the present invention.

Referring to FIGS. 3-11, a second embodiment of a system is provided that enables both primary and secondary imaging as well as magnetic navigational control within a subject's body. The system comprises magnetic navigational equipment 22 that may be moved from a first navigational position to a second position for enabling secondary imaging equipment to have access to the operating region of the subject's body, for example, during a procedure where additional views of the patient are required for the procedure. The system generally comprises a first imaging equipment support structure 24 having a generally C-shaped configuration, and a second imaging equipment support structure 26 having a generally C-shaped configuration. The first and second C-arm structures 24 and 26 are preferably mounted on tracks 38 and 40 that enable the first and second C-arms 24 and 26 to rotate in a generally circumferential arc about an operating region 28 of the subject's body as shown in FIG. 3.

In the second embodiment, the system comprises a first C-arm 24 with an imaging beam source 30 and an imaging beam receiver 32 that are mounted on the first C-arm 24 and positioned to be disposed on opposite sides of the operating region 28 for imaging the operating region. The imaging beam receiver 32 may be configured to accommodate an imaging plate of approximately 20 centimeters, and may preferably accommodate an imaging plate of up to approximately 30 centimeters, as shown by the region 29 in FIG. 7. The operating region 28 is represented by a sphere of approximately 12 inch diameter as shown in FIG. 1, which represents a patient's head plus 1 inch of additional clearance. The system also comprises a second C-arm 26 with an imaging beam source 34 and an imaging beam receiver 36 that are mounted on the second C-arm 26. The imaging beam source 34 and receiver 26 are positionable to be disposed on opposite sides of the operating region 28 to image the operating region. The first C-arm 24 and second C-arm 26 are movably mounted via tracks 38 and 40, to permit coordinated simultaneous rotation of the first C-arm 24 and the second C-arm 26 in a generally circumferential arc about the operating region 28 of the subject's body as shown in FIG. 1. The first and second C-arms may be controllably rotated about the patient by a servo drive motor mechanisms preferably controlled by a computer system that is integrated with both the imaging and navigational equipment. In this manner, the computer control of the imaging and navigational equipment may provide for seamless coordination of movement of both systems to provide either imaging operation, navigation control or both.

The second C-arm 26 is movable between an imaging position and a navigating position. In the navigating position, a pair of magnetic pods 22 are disposed on opposite sides of and projecting towards the operating region 28, in the same plane as the imaging beam source 30 and the imaging beam receiver 32 mounted on the first C-arm. The pair of magnetic pods 22 are mounted on the second C-arm 24 in a manner such that they extend from the second C-arm towards the patient. The magnetic pods 22 are capable of applying a navigating magnetic field of at least 0.8 T in any direction to the operating region 28. The pair of magnetic navigation equipment pods 22 are preferably positioned relative to each other to provide a 12 inch pod-to-pod separation, which spacing provides for INR or Neurosurgery therapies. The magnetic pods 22 each have a weight of approximately 120 pounds. In the imaging position, the imaging beam source 34 and imaging beam receiver 36 on the second C-arm 26 are positioned so that the imaging beam sources 30, 34 and receivers 32, 36 on both the first C-arm 24 and second C-arm 26 are in the same plane. The second C-arm 26 accordingly is movable from a navigating position to a secondary imaging position in as little as 10 seconds.

The second C-arm 26 provides a minimum articulation of the magnetic pods 22 to ensure compatibility with secondary imaging equipment. The second C-arm 26 is preferably translatable between an extended position and a retracted position, by virtue of a ceiling track 42 extending above the patient support table 44. In one position, the second C-arm 26 is extended such that the magnetic pods 22 are moved into the plane comprising the imaging beam source on the first C-arm, to enable magnetic navigation in the operating region 28. The magnetic pods 22 mounted on the second C-arm are positioned so that, in their navigating position, a line between the magnetic pods 22 is generally perpendicular to, and coplanar with a line between the imaging beam source 30 and the imaging beam receiver 32 mounted on the second C-arm 24. the second C-arm is retracted such that the magnetic pods 22 are moved out of the plane to accommodate the imaging beam source 34 and imaging beam receiver 36 on the second C-arm in its imaging position. In the second secondary imaging position, the line between the imaging beam source 34 and imaging beam receiver 36 on the second C-arm 26 is generally perpendicular to, and coplanar with a line between the imaging beam source 30 and imaging beam receiver 32 on the first C-arm.

The first C-arm 24 is preferably mounted on a track 38 for enabling the C-arm to rotate about the radial center of the first C-arm 24, such that the first C-arm 24 rotates in a generally circumferential arc about the operating region 28. The track 38 is preferably mounted to a base unit having a drive mechanism for controlling the rotation of the first C-arm 24 about the operating region. The base unit for the first C-arm may be positioned on the floor in a location relative to a horizontal support table 44 for the patient, such that the longitudinal axis of the patient is within the operating region 28. In the first embodiment, a standing C-arm imaging system is provided as shown in FIG. 3. The C-arm shown is a standing Siemens C-arm imaging system, but may alternatively be any equivalent imaging system capable of rotation about an operating region of a patient. The horizontal support table 42 may also be moved in a direction along the longitudinal axis of the patient, to position a desired area of the subject's body within the operating region 28.

The second embodiment further comprises a second C-arm 26 that is mounted on a track support 40 for enabling the second C-arm to rotate about the radial center of the second C-arm 24. The second C-arm 24 rotates in a generally circumferential arc about the operating region 28. The second C-arm 26 shown in FIG. 3 is preferably an overhead secondary Siemens C-arm, but may alternatively be any equivalent system capable of rotation about an operating region of a patient. The track support 40 is preferably mounted via a motorized trolley or travel mechanism to an overhead linear track that is parallel to the longitudinal axis of the patient and/or support table. The overhead linear track enables the second C-arm 26 to be moved to a first imaging position, where a line between the imaging beam source 34 and receiver 36 on the second C-arm 26 is generally perpendicular to, and coplanar with a line between the imaging beam source 30 and imaging beam receiver 32 on the first C-arm 24. The second C-arm 26 can also be moved to a second navigating position, where a line between the pair of magnetic navigational pods 22 on the second C-arm 26 is generally perpendicular to, and coplanar with a line between the imaging beam source 30 and imaging beam receiver 32 on the first C-arm 24. Thus, the second C-arm 26 can provide for secondary imaging of the operating region that may be required during a procedure in which a medical device is being magnetically navigated within the subject's body.

Figure 12:
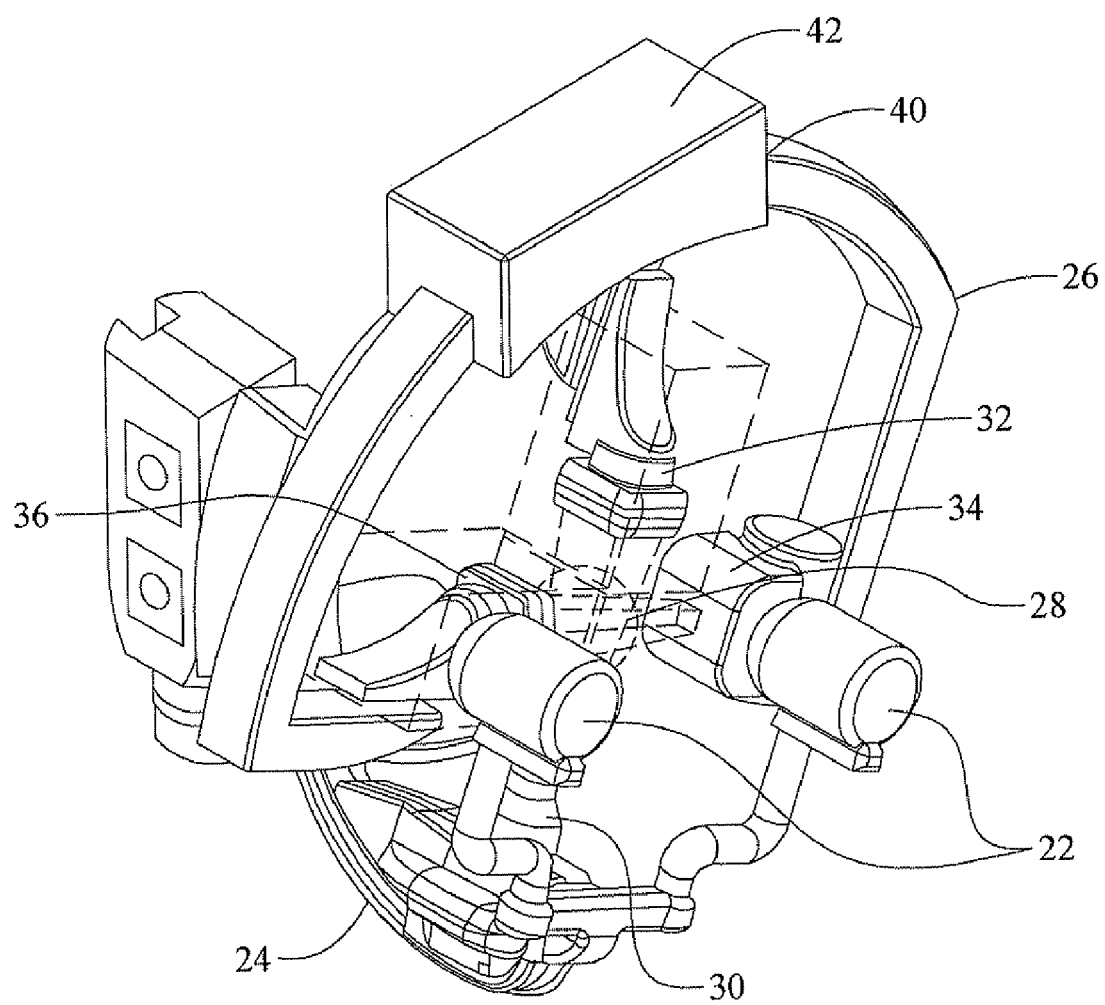
FIG. 12 is an isometric view of a third embodiment of a magnetic navigation and imaging system in accordance with the present invention.
Figure 13:
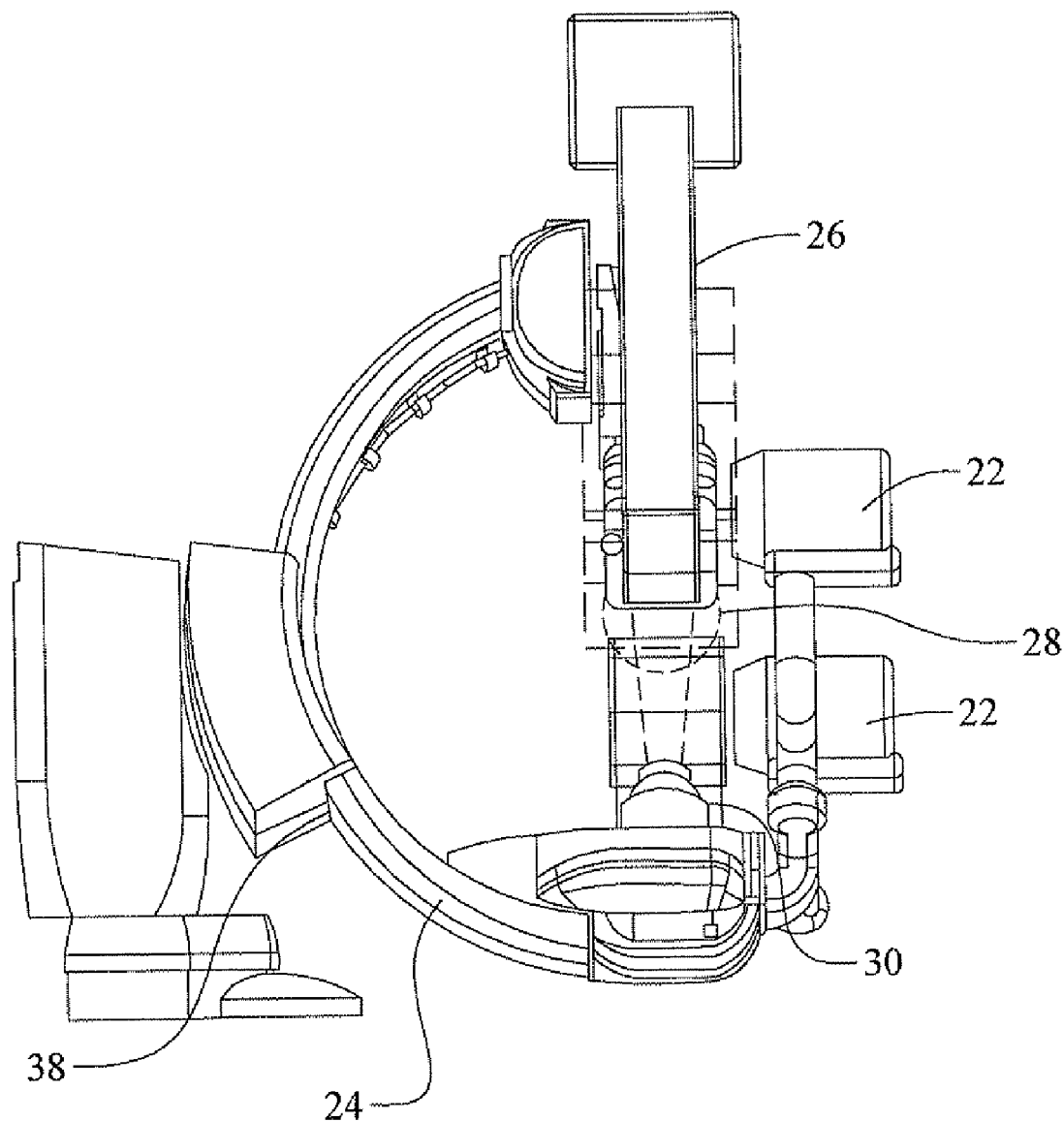
FIG. 13 is a left side elevation view of the system of the third embodiment, showing the imaging beam and imaging receiver on the first C-arm in the same plane as the imaging beam and receiver on the second C-arm, with the magnet pods moved out of the plane.
Figure 14:
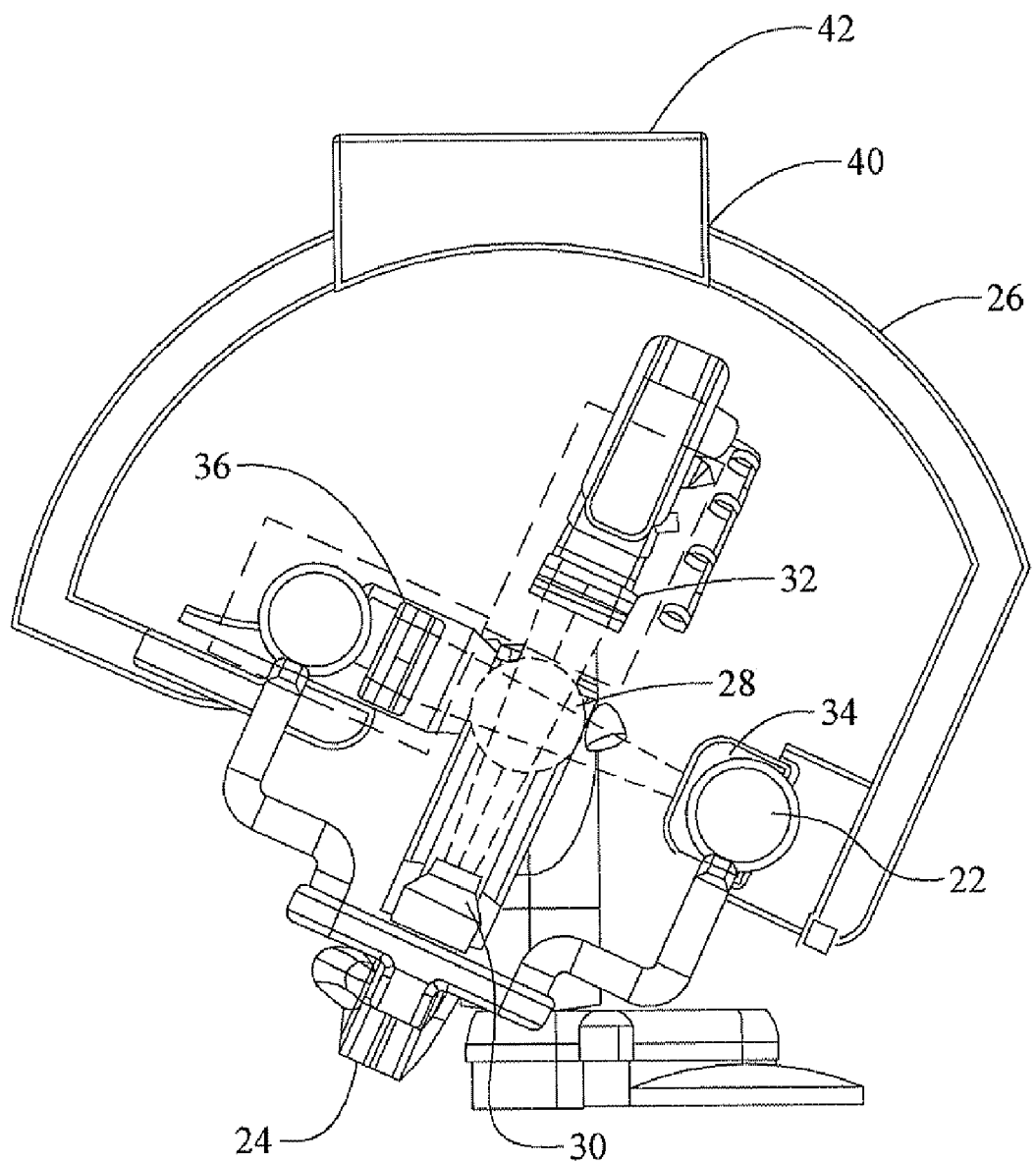
FIG. 14 is a front elevation view of the system of the third embodiment, showing the imaging beam on the first C-arm and the imaging beam on the second C-arms perpendicular to each other and aligned with the patient.
Figure 15:
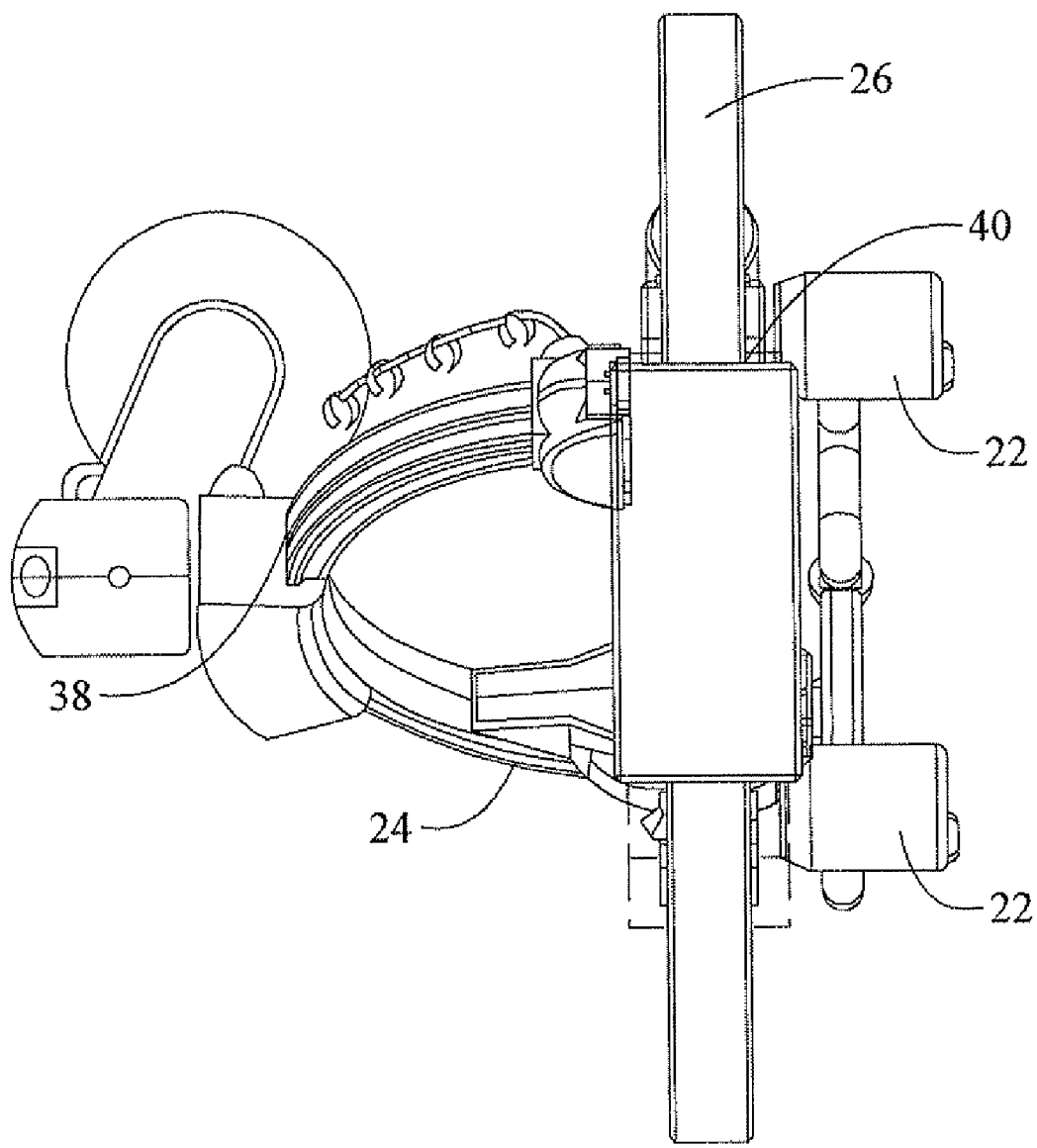
FIG. 15 is a top elevation view of the system of the third embodiment.
Figure 16:
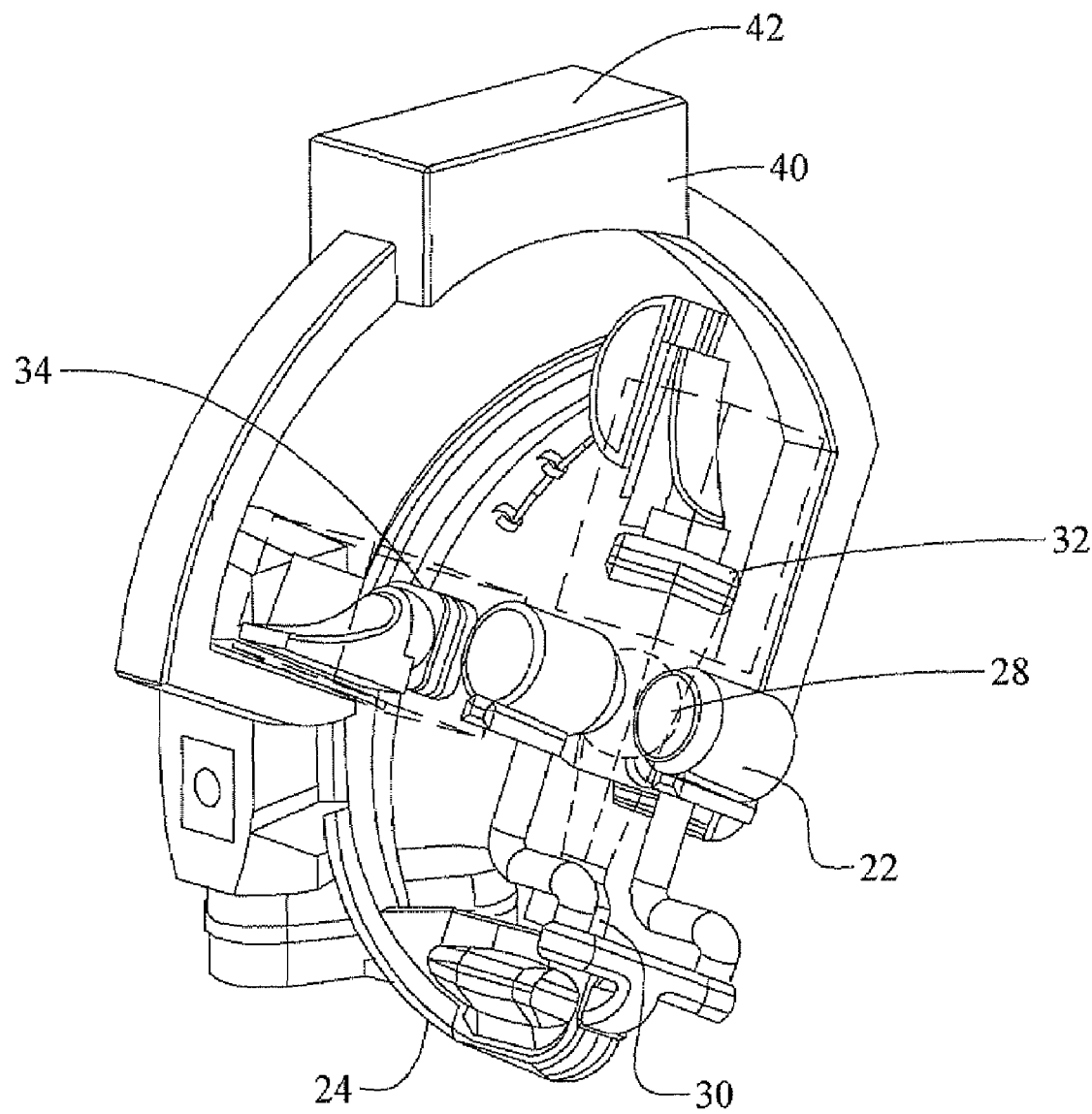
FIG. 16 is an isometric view of the imaging beam and receiver of the first C-arm on both sides of the patient's body, and perpendicular to the navigational magnet pods.
Figure 17:
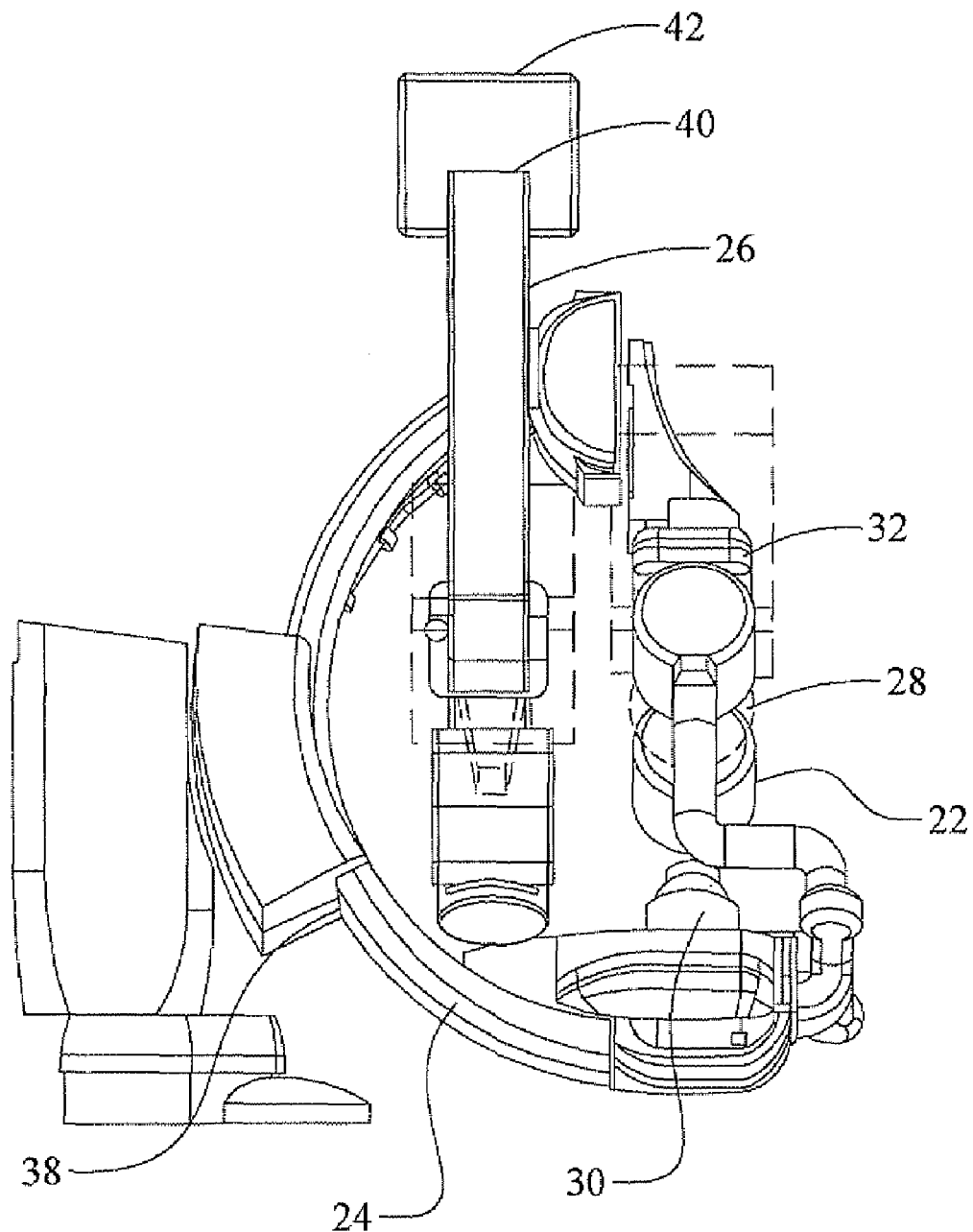
FIG. 17 is a side elevation view of the system shown in FIG. 16.
Figure 18:
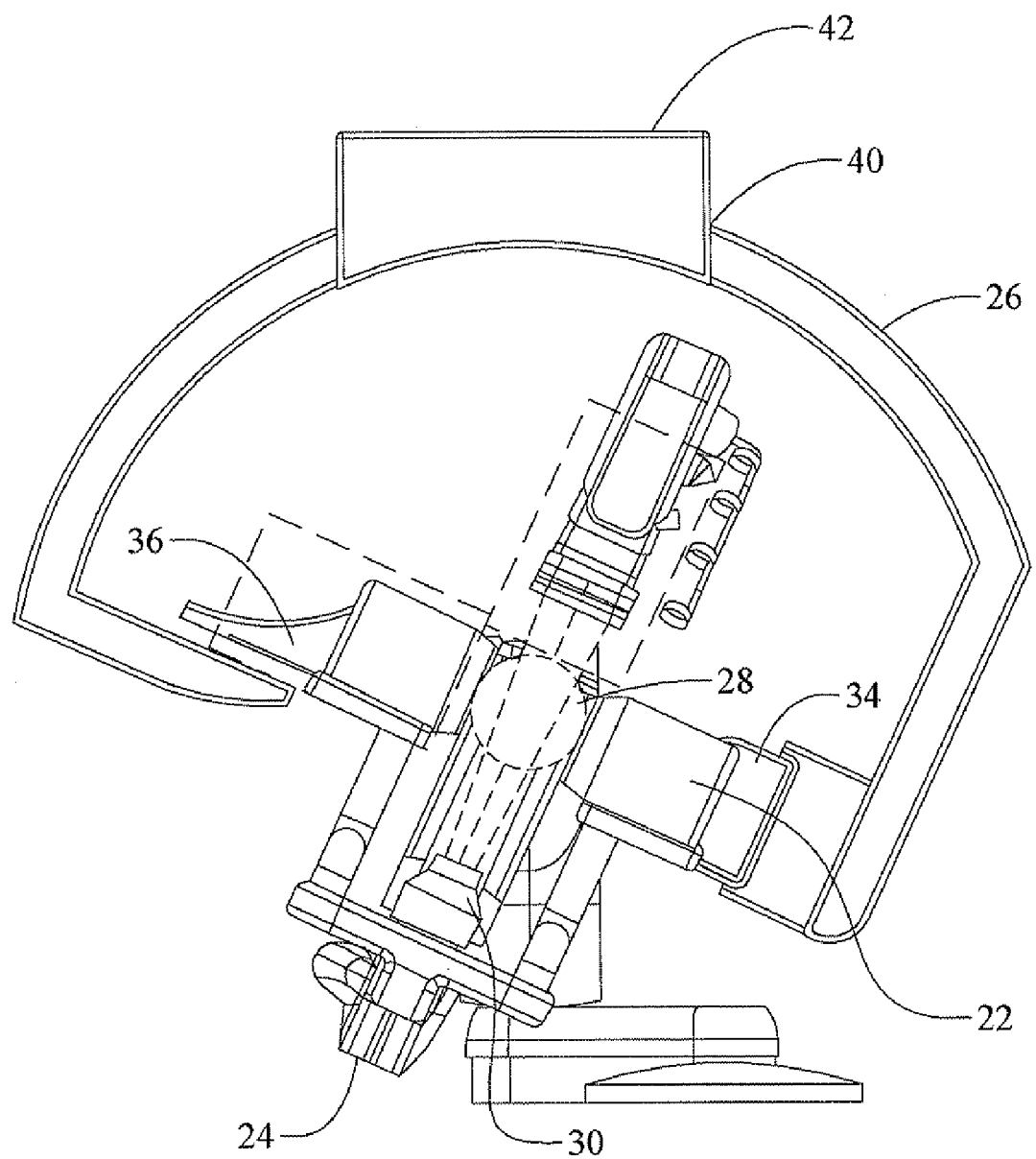
FIG. 18 is a front elevation view of the system shown in FIG. 16 in accordance with the present invention.

Referring to FIGS. 12-18, a third embodiment of a system is provided that also enables both primary and secondary imaging as well as magnetic navigational control within a subject's body. The system comprises magnetic navigational equipment 22 that may be moved from a first navigational position to a second position for enabling secondary imaging equipment to have access to the operating region of the subject's body, for example, during a procedure where additional views of the patient are required for the procedure. The system generally comprises a first imaging equipment support structure 24 having a generally C-shaped configuration, and a second imaging equipment support 26 structure having a generally C-shaped configuration 26. The first and second C-arm structures 24 and 26 are preferably mounted on tracks that enable the C-arms to rotate in a generally circumferential arc about an operating region 28 of the subject's body as shown in FIG. 12. In the third embodiment, the system comprises a first C-arm 24 with an imaging beam source 30 and an imaging beam receiver 32 that are mounted on the first C-arm 24 and positioned to be disposed on opposite sides of the operating region 28 for imaging the operating region. The imaging beam receiver 32 may be configured to accommodate an imaging plate of approximately 20 centimeters, and may preferably accommodate an imaging plate of up to approximately 30 centimeters. The operating region 28 is represented by a sphere of approximately 12 inch diameter as shown in FIG. 1, which represents a patient's head plus 1 inch of additional clearance. The system also comprises a second C-arm 26 with an imaging beam source 34 and an imaging beam receiver 36 that are mounted on the second C-arm 26. The imaging beam source 34 and imaging receiver 36 are positionable to be disposed on opposite sides of the operating region 28 for imaging the operating region. The first C-arm 24 and second C-arm 26 are movably mounted via tracks 38 and 40, to permit coordinated simultaneous rotation of the first C-arm 24 and the second C-arm 26 in a generally circumferential arc about the operating region 28 of the subject's body as shown in FIG. 1. The first and second C-arms may be controllably rotated about the patient by a servo drive motor mechanisms preferably controlled by a computer system that is integrated with both the imaging and navigational equipment. In this manner, the computer control of the imaging and navigational equipment may provide for seamless coordination of movement of both systems to provide either imaging operation, navigation control or both.

The second C-arm 26 is movable between an imaging position and a stowed position. In the imaging position, the imaging beam source 34 and imaging beam receiver 36 on the second C-arm 26 are positioned so that the imaging beam sources 30, 34 and receivers 32, 36 on both the first C-arm 24 and second C-arm 26 are in the same plane. In the stowed position, the second C-arm 26 is retracted away from the plane via a ceiling track 42, to provide accessibility for the magnetic navigation pods 22 on the first C-arm 24. The pair of magnetic pod units 22 are rotated or aligned to project towards the operating region. The pair of magnetic pods 22 are movably mounted on the first C-arm 24, such that the pods may be switched between a navigating position and a stowed position. In navigating position, the pods 22 are disposed on opposite sides of the operating region 28 in the same plane as the imaging beam source 30 and the imaging beam receiver 32 mounted on the first C-arm. The magnetic pods 22 are capable of applying a navigating magnetic field of at least 0.8 T in any direction to the operating region 28. The pair of magnetic pods 22 are preferably positioned relative to each other to provide a 12 inch pod-to-pod separation. Such separation permits the magnetic navigation equipment to be utilized for INR or Neurosurgery therapies. The magnetic pods 22 each have a weight of approximately 120 pounds.

The first C-arm 24 provides a minimum articulation of the magnetic pods 22 to ensure compatibility with secondary imaging equipment on the second C-arm 26. In the stowed position, the magnetic pods 22 are moved out of the plane comprising the imaging beam source on the first C-arm, to provide accessibility for the imaging beam source 34 and imaging beam receiver 36 on the second C-arm 26 to move into an imaging position. The magnetic pods 22 are preferably able to pivot or rotate away from the patient to provide a separation of at least 30 inches to accommodate positioning of the patient between the primary and secondary imaging sources. The imaging beam source 30 and the imaging beam receiver 32 mounted on the first C-arm 24 are positioned so that a line between the imaging beam source 30 and receiver 32 is generally perpendicular to, and coplanar with a line between the magnet pods 22 in their navigating position. In the secondary imaging position, the line between the imaging beam source 30 and receiver 32 on the first C-arm 24 is generally perpendicular to, and coplanar with a line between the imaging beam source 34 and imaging beam receiver 36 on the second C-arm 26.

The first C-arm 24 is preferably mounted on a track 38 for enabling the C-arm to rotate about the radial center of the first C-arm 24, such that the first C-arm 24 rotates in a generally circumferential arc about the operating region 28. The track 38 is preferably mounted to a base unit having a drive mechanism for controlling the rotation of the first C-arm 24 about the operating region. The base unit for the first C-arm may be positioned on the floor in a location relative to a horizontal support table 44 for the patient, such that the longitudinal axis of the patient is within the operating region 28. In the first embodiment, a standing C-arm imaging system is provided as shown in FIG. 12. The C-arm shown is a standing Siemens C-arm imaging system, but may alternatively be any equivalent imaging system capable of rotation about an operating region of a patient. A neuro-navigation system is integrated with the C-arm in a pivotal arrangement, where the first C-arm 24 comprises two magnetic pods 22 mounted on extension arms 46 that are pivotally secured to the first standing C-arm. The magnetic pods 22 may swivel or rotate on the first C-arm away from the operating region of the patient. When pivoted away from the patient, access is provided for a second C-arm 26 that may be moved into alignment with the first standing C-arm to permit secondary imaging of the operating region of the patient. The horizontal support table 44 may also be moved in a direction along the longitudinal axis of the patient, to position a desired area of the subject's body within the operating region 28.

The third embodiment further comprises a second C-arm 26 that is mounted on a track support 40 for enabling the second C-arm to rotate about the radial center of the second C-arm 24. The second C-arm 24 rotates in a generally circumferential arc about the operating region 28. The track support 40 is preferably mounted via a motorized trolley or travel mechanism to an overhead linear track 42 that is parallel to the longitudinal axis of the patient and/or support table 44. The overhead linear track 42 enables the second C-arm 26 to be moved to a secondary imaging position, such that a line between the imaging beam source 30 and receive 32 on the first C-arm 24 is generally perpendicular to, and coplanar with a line between the imaging beam source 34 and imaging beam receiver 36 on the second C-arm 26. The second C-arm 26 shown in FIG. 12 is preferably an overhead secondary Siemens C-arm, but may alternatively be any equivalent system capable of rotation about an operating region of a patient. Thus, the second C-arm can provide for secondary imaging of the operating region that may be required during a procedure in which a medical device is being magnetically navigated within the subject's body.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A system for imaging and magnetically navigating a medical device within an operating region in a subject's body, the system comprising: a first C-arm; a first imaging beam source and a first imaging beam receiver mounted on the first C-arm and positioned to be disposed on opposite sides of the operating region to image the operating region; a second C-arm; a second imaging beam source and a second imaging beam receiver mounted on the second C-arm and positionable to be disposed on opposite sides of the operating region to image the operating region; the second C-arm being movable between an imaging position in which the second imaging beam source and second imaging beam receiver on the second C-arm are positioned so that the first and second imaging beam sources and first and second imaging beam receivers are in the same plane, and a stowed position in which the second C-arm is in a navigating position; and a pair of magnetic pods movably mounted on the first C-arm, the magnetic pods being movable between a navigating position in which the pods are disposed on opposite sides of the operating region in the same plane as the second imaging beam source and the second imaging beam receiver, for applying a navigating magnetic field of at least 0.08 T in any direction to the operating region, and a stowed position in which the magnets are moved out of the plane to accommodate the second imaging beam source and second imaging beam receiver on the second C-arm in its imaging position.

2. The system according to claim 1 wherein the first imaging beam source and the first imaging beam receiver are positioned so that a line between the first imaging beam source and first imaging beam receiver is generally perpendicular to, and coplanar with a line between the magnet pods in their navigating position.

3. The system according to claim 2 wherein the second imaging beam source and the second imaging beam receiver on the second C-arm are positioned so when the second C-arm is in its imaging position, a line between the second imaging beam source and second imaging beam receiver is generally perpendicular to, and substantially coplanar with a line between the first imaging beam source and first imaging beam receiver on the first C-arm.

4. The system according to claim 1 wherein the first C-arm is mounted on the floor.

5. The system according to claim 1 further comprising a patient support having a head and a foot, and wherein the first C-arm is positioned at the head.

6. The system according to claim 5 wherein the second C-arm moves toward and away from the patient in a direction parallel to the patients longitudinal axis.

7. The system according to claim 1 wherein the magnet pods pivot about an offset axis to move out of the plane with the first imaging beam source and first imaging beam receive on the first C-arm, to accommodate movement of the second C-arm.

8. The system according to claim 1 wherein the magnetic pods translate to accommodate movement of the second C-arm.

9. A system for imaging and magnetically navigating a magnetically responsive medical device within an operating region in a subject's body, the system comprising: a first C-arm; a first imaging beam source and a first imaging beam receiver mounted on the first C-arm so that the first imaging beam source and first imaging beam receiver can be disposed on opposite sides of the operating region in the subject; a second C-arm, movable relative to the first C-arm between a stowed position and an imaging position; a second imaging beam source and a second imaging beam receiver mounted on the second C-arm so that when the second C-arm is in its imaging position, the second imaging beam source and second imaging beam receiver can be disposed on opposite sides of the operating region, in substantially the same plane as the first imaging beam source and first imaging beam receiver on the first C-arm; a pair of magnetic pods movably mounted on the first C-arm, the magnetic pods being movable between a navigating position in which the pods are disposed on opposite sides of the operating region in the same plane as the second imaging beam source and the second imaging beam receiver, for applying a navigating magnetic field of at least 0.08 T in any direction to the operating region, and a stowed position in which the magnets are not on opposite sides of the operating region to accommodate the second imaging beam source and second imaging beam receiver on the second C-arm in its imaging position.

10. The system according to claim 9 wherein the first imaging beam source and the first imaging beam receiver are positioned so that a line between the first imaging beam source and first imaging beam receiver is generally perpendicular to, and coplanar with a line between the magnet pods in their navigating position.

11. The system according to claim 10 wherein the second imaging beam source and the second imaging beam receiver on the second C-arm are positioned so when the second C-arm is in its imaging position, a line between the second imaging beam source and second imaging beam receiver is generally perpendicular to, and substantially coplanar with a line between the first imaging beam source and first imaging beam receiver.

12. The system according to claim 9 wherein the first C-arm is mounted on the floor.

13. The system according to claim 9 further comprising a patient support having a head and a foot, and wherein the first C-arm is positioned at the head.

14. The system according to claim 13 wherein the second C-arm moves toward and away from the patient in a direction parallel to the patients longitudinal axis.

15. The system according to claim 9 wherein the magnet pods pivot about an offset axis to move out of the plane with the first imaging beam source and first imaging beam receive on the first C-arm, to accommodate movement of the second C-arm.

16. The system according to claim 9 wherein the magnetic pods translate to accommodate movement of the second C-arm.

17. A system for imaging, and magnetically navigating a magnetically responsive medical device within an operating region in a subject's body, the system comprising: a first C-arm; a first imaging beam source and a first imaging beam receiver mounted on the first C-arm so that the first imaging beam source and first imaging beam receiver can be disposed on opposite sides of the operating region in the subject; a second C-arm, movable relative to the first C-arm between an imaging position and a navigating position; a second imaging beam source and a second imaging beam receiver mounted on the second C-arm so that when the second C-arm is in its imaging position, the second imaging beam source and second imaging beam receiver can be disposed on opposite sides of the operating region, in substantially the same plane as the first imaging beam source and first imaging beam receiver on the first C-arm; a pair of magnetic pods mounted on the second C-arm, the magnetic pods being positioned on the C-arm so that when the second C-arm is in its navigation position, the magnetic pods are disposed on opposite sides of the operating region in the same plane as the second imaging beam source and the second imaging beam receiver on the first C-arm, for applying a navigating magnetic field of at least 0.08 T in any direction to the operating region.

18. The system of claim 17 wherein the second imaging beam source and the second imaging beam receiver on the second C-arm are positioned so when the second C-arm is in its imaging position, a line between the second imaging beam source and second imaging beam receiver is generally perpendicular to, and substantially coplanar with a line between the first imaging beam source and first imaging beam receiver on the first C-arm.

19. The system according to claim 17 wherein the second C-arm moves toward and away from the patient in a direction parallel to the patients longitudinal axis.

20. The system of claim 19 wherein the magnet pods are generally adjacent to the second imaging beam source and second imaging beam receiver mounted on the second C-arm, such that the second C-arm may move from a navigation position in which the magnet pods are disposed on opposite sides of the operating region in the same plane as the first imaging beam source and the first imaging beam receiver on the first C-arm, and an imaging position in which the second imaging beam source and second imaging beam receiver mounted on the second C-arm are disposed on opposite sides of the operating region in the same plane as the first imaging beam source and the first imaging beam receiver on the first C-arm.

* * * * *

UNITED STATES PATENT AND TRADEMARK OFFICE
CERTIFICATE OF CORRECTION

PATENT NO. : 7,603,905 B2
APPLICATION NO. : 11/483397
DATED : October 20, 2009
INVENTOR(S) : Francis M. Creighton, IV It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 668 days.

Signed and Sealed this

Fifth Day of October, 2010

David J. Kappos
*Director of the United States Patent and Trademark Office*